United States Patent [19]

Lorquet

[11] 4,209,470
[45] Jun. 24, 1980

[54] PROCESS FOR THE SEPARATION OF HYDROGEN FLUORIDE FROM ITS MIXTURES WITH 1-CHLORO-1,1-DIFLUOROETHANE

[75] Inventor: Robert Lorquet, Rixensart, Belgium

[73] Assignee: Solvay & Cie, Brussels, Belgium

[21] Appl. No.: 2,449

[22] Filed: Jan. 10, 1979

[30] Foreign Application Priority Data

Jan. 13, 1978 [FR] France ................. 78 01309

[51] Int. Cl.$^2$ ................................................ C07C 7/02
[52] U.S. Cl. .............................. 260/652 P; 260/653; 423/240
[58] Field of Search .................. 260/652 P, 653; 423/240 R

[56] References Cited

U.S. PATENT DOCUMENTS

| 2,894,044 | 7/1959 | Prill | 260/653.7 |
|---|---|---|---|
| 3,442,961 | 5/1969 | Hutton | 260/653.3 |
| 3,696,156 | 10/1972 | Weaks | 260/653 |
| 3,873,629 | 3/1975 | Jones | 260/653 |
| 4,102,981 | 7/1978 | Woychesin et al. | 260/652 P |
| 4,157,380 | 6/1979 | Prahl | 423/240 |

FOREIGN PATENT DOCUMENTS

47/39086 10/1972 Japan.
49/3965 1/1974 Japan.
1323234 7/1973 United Kingdom.

Primary Examiner—C. Davis
Attorney, Agent, or Firm—Spencer & Kaye

[57] ABSTRACT

Process for the separation of hydrogen fluoride from its mixtures with 1-chloro-1,1-difluoroethane, such as those obtained in the manufacture of the latter. An auxiliary solvent, chosen from among 1,1-dichloro-1-fluoroethane, vinylidene chloride, 1,1,1-trichloroethane and mixtures thereof, is added to the mixture so as to obtain two separate liquid phases, one of which contains the hydrogen fluoride and the other of which contains the 1-chloro-1,1-difluoroethane. Virtually all the hydrogen fluoride is recovered in the anhydrous form in the manufacture of monomers such as vinylidene fluoride, from chlorohydrocarbons such as vinylidene chloride and 1,1,1-trichloroethane.

12 Claims, 4 Drawing Figures

4,209,470

PROCESS FOR THE SEPARATION OF HYDROGEN FLUORIDE FROM ITS MIXTURES WITH 1-CHLORO-1,1-DIFLUOROETHANE

BACKGROUND OF THE INVENTION

The invention relates to a process for the separation of hydrogen fluoride from its mixtures with 1-chloro-1,1-difluoroethane, and more particularly, it relates to the separation of the unconverted hydrogen fluoride which is present in the mixtures resulting from the manufacture of 1-chloro-1,1-difluoroethane by the hydrofluorination of chlorohydrocarbons. The present invention applies very particularly to the separation of the hydrogen fluoride present in the mixtures based on 1-chloro-1,1-difluoroethane which results from the hydrofluorination of vinylidene chloride or 1,1,1-trichloroethane.

Most of the processes for the manufacture of 1-chloro-1,1-difluoroethane by hydrofluorination give complex mixtures which contain, in particular, 1-chloro-1,1-difluoroethane and unconverted hydrogen fluoride. This applies to the process for the manufacture of 1-chloro-1,1-difluoroethane by the hydrofluorination of vinylidene chloride or 1,1,1-trichloroethane.

In order to separate pure 1-chloro-1,1-difluoroethane from these mixtures, they are commonly washed with an aqueous phase (British Pat. No. 1,323,234 filed on July 27, 1971 in the name of Daikin Kogyo Co. Ltd.) which can contain an acid or a base (Japanese Patent Application No. 47/39,086 filed on Aug. 31, 1964 in the name of Kureha Chemical Ind. Co. Ltd.)

These known processes exhibit the serious disadvantage that they recover the hydrogen fluoride in the form of aqueous solutions of inorganic fluorides or of hydrofluoric acid.

In fact, in order to obtain an adequate degree of conversion of the starting chlorohydrocarbon, it is necessary to employ, in the hydrofluorination, a large excess of hydrogen fluoride. It is highly desirable, for economic reasons, to recover the large excess of hydrogen fluoride in the anhydrous form so that it can be recycled into the reaction.

Simple distillation, which has already been proposed for the separation of mixtures of hydrogen fluoride with 1,1-dichloro-1-fluoroethane as described in U.S. Pat. No. 2,894,044 filed on Feb. 16, 1956 by Monsanto Chemical Co., cannot be employed for the purpose of recovering hydrogen fluoride in the anhydrous form, because hydrogen fluoride and 1-chloro-1,1-difluoroethane form an azeotrope. Furthermore, separation by decantation cannot be contemplated in view of the high mutual solubilities of hydrogen fluoride and 1-chloro-1,1-difluoroethane.

SUMMARY OF THE PRESENT INVENTION

There has now been found in accordance with the present invention a process which no longer has the above-mentioned disadvantages of the processes of the prior art.

The present invention therefore relates to a process for the separation of hydrogen fluoride from its mixtures with 1-chloro-1,1-difluoroethane, in accordance with which the liquid mixture is separated by decantation so as to obtain a liquid organic phase enriched in 1-chloro-1,1-difluoroethane and a liquid inorganic phase enriched in hydrogen fluoride, and in accordance with which a liquid containing an auxiliary solvent, selected from the group consisting of 1,1-dichloro-1-fluoroethane, vinylidene chloride, 1,1,1-trichloroethane and mixtures thereof, is added to the mixture before subjecting it to decantation.

DETAILED DESCRIPTION OF THE INVENTION

Figure 1:
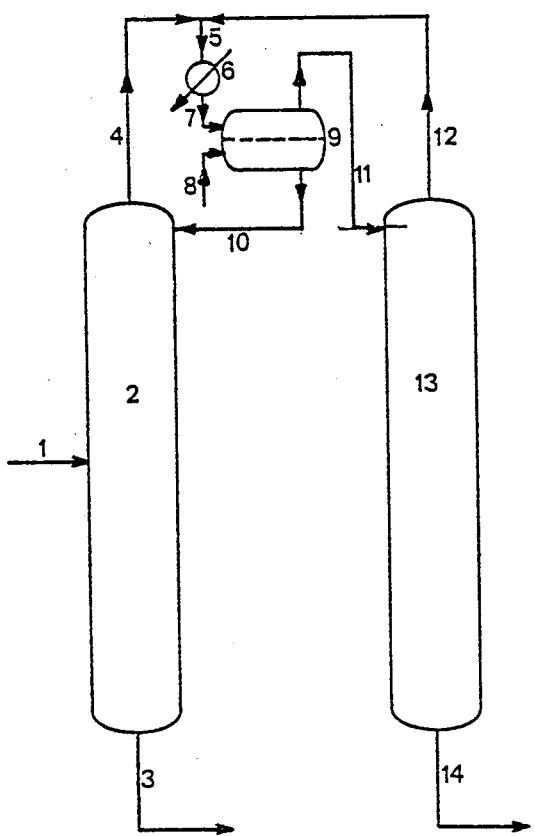
FIG. 1 shows a schematic flow diagram of the process of the present invention using distillation columns having a column condenser and a decanter.

The liquids added according to the present invention can be pure products or mixtures. They generally comprise to the extent of at least 20% by weight of auxiliary solvents, excellent results being obtained when they comprise to the extent of at least 50% by weight of auxiliary solvents. Of course, the best results are obtained when the liquid added is formed exclusively from these auxiliary solvents. However, for reasons of simplification of the process, as will become apparent later, liquids containing from 50 to 100% by weight of auxiliary solvents are most frequently used.

When the mixture to be treated originates from the hydrofluorination of vinylidene chloride, it is preferred to employ liquids containing 1,1-dichloro-1-fluoroethane and vinylidene chloride as the only auxiliary solvents. Likewise, when the mixture to be treated originates from the hydrofluorination of 1,1,1-trichloroethane, it is preferred to employ liquids containing 1,1-dichloro-1-fluoroethane and 1,1,1-trichloroethane as the only auxiliary solvents. In all cases, the best results are obtained when the auxiliary solvents comprise at least 50%, and preferably at least 80%, by weight of 1,1-dichloro-1-fluoroethane, relative to the total weight amount of the auxiliary solvents.

In addition to the auxiliary solvents, the liquids added according to the present invention can also contain hydrogen fluoride and 1-chloro-1,1-difluoroethane without any disadvantage. These compounds are generally present in an amount of less than 80%, and preferably less than 50% by weight. Thus, liquids which can be used are reaction mixtures originating from the hydrofluorination of vinylidene chloride or of 1,1,1-trichloroethane, from which mixtures the hydrogen chloride by-product has optionally been removed, and which contain large amounts of intermediate (1,1-dichloro-1-fluoroethane), variable amounts of starting organic reactant (vinylidene chloride or 1,1,1-trichloroethane) and smaller amounts of product (1-chloro-1,1-difluoroethane) and of hydrogen fluoride. Of course, it is also possible to use purified products and mixtures originating from various separation treatments to which the reaction mixtures can be subjected.

The amount of liquid to be added can vary within fairly wide limits. In general, the liquid added is employed in proportions such that the auxiliary solvents (1,1-dichloro-1-fluoroethane, vinylidene chloride and 1,1,1-trichloroethane) are present in an amount of 0.01 to 5, and preferably 0.05 to 2.5, mols of auxiliary solvent per mol of 1-chloro-1,1-difluoroethane which is present in the complex mixture subjected to decantation. The complex mixture subjected to decantation comprises the mixture to be treated and the liquid added. Amounts of between 0.1 and 1 mol per mol are particularly suitable. For certain applications, where it is not essential to greatly reduce the content, in one another, of hydrogen fluoride and of 1-chloro-1,1-difluoroethane respectively, smaller amounts of auxiliary solvent can be employed. It is also possible to employ larger amounts of auxiliary solvent, but, from an economic point of view, this method of operation is less valuable because the liquid organic phase must subsequently be distilled in order to separate off the 1-chloro-1,1-difluoroethane. Furthermore, the advantage which results from the reduction in the solubility of the hydrogen fluoride in the organic phase, when employing very large amounts of auxiliary solvent, is at least partially compensated by the fact that the total amount of hydrogen fluoride dissolved in the organic phase is of course proportional to the volume of this phase.

The process according to the present invention is suitable for treating mixtures which contain a preponderant amount of hydrogen fluoride and of 1-chloro-1,1-difluoroethane in any relative proportions. It is particularly suitable for mixtures containing from 0.1 to 50 mols of hydrogen fluoride per mol of 1-chloro-1,1-difluoroethane. Excellent results have been obtained by treating, in accordance with the process of the present invention, mixtures containing from 0.2 to 10 mols of hydrogen fluoride per mol of 1-chloro-1,1-difluoroethane.

The mixtures of hydrogen fluoride and 1-chloro-1,1-difluoroethane which can be treated can also contain other compounds. Among these, 1,1-dichloro-1-fluoroethane, vinylidene chloride and 1,1,1-trichloroethane are obviously not troublesome; indeed the contrary is true, and it is advantageous to take their possible presence into account when evaluating the amount of auxiliary solvent to be added. The process according to the invention can generally be applied to mixtures containing at least 50% by weight of hydrogen fluoride and of 1-chloro-1,1-difluoroethane. It is preferably applied to mixtures containing at least 80% by weight of these compounds, the best results being obtained when they contain only these compounds. Hydrogen chloride and halogenohydrocarbons containing from 1 to 6 carbon atoms are most frequently included among the other compounds which can be present in the mixture. However, when the starting mixture originates from the hydrofluorination of vinylidene chloride or of 1,1,1-trichloroethane, it is advantageous to remove at least part of the hydrogen chloride by-product from the mixture, for example by distillation, before treating it according to the present invention.

According to a preferred embodiment of the present invention, a mixture of 1-chloro-1,1-difluoroethane and hydrogen fluoride corresponding to their azeotropic composition is treated.

The mixtures of 1-chloro-1,1-difluoroethane and hydrogen fluoride to be treated according to the present invention are obtained in any conventional manner. In general, they originate from the hydrofluorination of vinylidene chloride or of 1,1,1-trichloroethane. In this case, it is advantageous to remove at least part of the hydrogen chloride by-product, for example by distillation, from the composition thus obtained, before treating it according to the present invention. This separation of the hydrogen chloride can preferably be followed by a separatiion of at least part of at least one of the constituents of the composition, which is chosen from among the unconverted reactants, the by-products of the reaction and, optionally, that constituent, chosen from among hydrogen fluoride and 1-chloro-1,1-difluoroethane, which is in excess relative to the azeotropic composition, so as to obtain the mixture to be treated according to the present invention.

The liquid can be added in the form of a gas or a liquid to the mixture to be treated, which itself may possibly be a gas or a liquid. After this addition, the complex mixture thus obtained is kept at a temperature and pressure which are chosen so as to keep the complex mixture in the form of a liquid or bring it into this form, for the purpose of separating the two liquid phases, which are organic and inorganic, by decantation. In general, the temperatures used do not exceed 110° C. and preferably do not exceed 90° C. Temperatures between $-50°$ and $+80°$ C. are successfully used. The pressure can be slightly less than, equal to or greater than atmospheric pressure. Pressures ranging from 0.8 to 30 kg/cm$^2$, and preferably from 1 to 20 kg/cm$^2$, are generally used.

The separation by decantation can be carried out continuously or discontinuously. It can be carried out in accordance with various techniques which are in themselves known, such as settling by gravity or by the action of a centrifugal force, or passage across porous membranes which are selectively wetted by one or other of the phases. Various types of apparatuses known in the art can be used for this purpose. Thus, florentine receivers, centrifugal separators, separating filters with membranes, or electrical separators can be used. The separation by decantation can be facilitated by a prior operation for the coalescence of the droplets in apparatuses known in the art, such as wads or cartridges made of fibrous materials which can preferably be wetted by the disperse phase.

The separation by decantation according to the present invention can advantageously be combined with other separation operations such as distillations. Thus, the hydrogen fluoride present in the liquid inorganic phase can be efficiently separated from the 1-chloro-1,1-difluoroethane by means of a distillation carried out under conditions which are suitable for the distillation of a mixture of liquids which are sparingly soluble in one another and form a minimum-boiling point azeotrope. Likewise, the 1-chloro-1,1-difluoroethane present in the liquid organic phase can be separated off by means of a similar distillation which makes it possible to collect, as the bottom product, an organic phase which is free from hydrogen fluoride and can be subjected to a second distillation in order to separate off the 1-chloro-1,1-difluoroethane.

In accordance with a preferred embodiment of the present invention, the separation by decantation is carried out in an ordinary condenser/decanter in which the top product from two distillations, which constitutes the mixture to be treated according to the present invention, is condensed, to which mixture the liquid containing an auxiliary solvent is added, and from which the liquid organic phase is withdrawn and fed into the reflux of one distillation, and the liquid inorganic phase is withdrawn and fed into the reflux of the other. The condenser/decanter can consist of a single apparatus in which the condensation and decantation operations take place simultaneously, or two successive separate apparatuses in which the two operations respectively take place separately.

A separation process of this kind preferably comprises the following operations:

(a) first distillation so as to obtain, at the top of the column, a mixture essentially containing hydrogen fluoride and 1-chloro-1,1-difluoroethane in proportions similar to those corresponding to the azeotrope and, at the bottom of the column, a first liquid fraction containing the constituent which, in the presence of all the products fed into the first distillation, is in excess relative to the azeotropic composition.

(b) separation by decantation into a liquid inorganic phase enriched in hydrogen fluoride and a liquid organic phase enriched in 1-chloro-1,1-difluoroethane, after condensation of the mixture collected at the top of the column and addition of the liquid containing an auxiliary solvent, (c) recycling, for return to the first distillation, of that liquid phase obtained from the separation by decantation which contains the constituent which, in the first distillation, is in excess relative to the azeotropic composition, and (d) second distillation of the other liquid phase obtained from the separation by decantation, so as to obtain, at the top of the column, a mixture which essentially contains hydrogen fluoride and 1-chloro-1,1-difluoroethane in proportions similar to those corresponding to the azeotrope, which mixture is subjected to condensation and separation by decantation in the same way as the top product from the first distillation, and at the bottom of the column, a second liquid fraction containing the constituent which, in the presence of all the products fed into the first distillation, is deficient relative to the azeotropic composition.

The expression "all the products fed into the first distillation" as used herein refers to the liquid phase obtained from decantation and which is recycled for return to the first distillation, and the other products which are optionally fed into this distillation.

The composition of the azeotrope of hydrogen fluoride with 1-chloro-1,1-difluoroethane, under a pressure of 5 kg/cm$^2$, is 38 to 48 mol % of hydrogen fluoride, according to Japanese Patent Application No. 49/125,286 filed on Apr. 6th, 1973 in the name of Daikin Kogyo Co. Ltd. If all the products fed into the first distillation contain less hydrogen fluoride than the azeotropic composition, that is to say less than about 40 mol % of hydrogen fluoride, the first liquid fraction collected as the bottom product from the first distillation contains 1-chloro-1,1-difluoroethane and is virtually free from hydrogen fluoride, and the second liquid fraction collected as the bottom product from the second distillation contains hydrogen fluoride and is virtually free from 1-chloro-1,1-difluoroethane. In the opposite case, that is to say if all the products fed into the first distillation contain more than about 40 mol % of hydrogen fluoride, the first liquid fraction collected as the bottom product from the first distillation contains hydrogen fluoride and is virtually free from 1-chloro-1,1-difluoroethane, and the second liquid fraction collected as the bottom product from the second distillation contains 1-chloro-1,1-difluoroethane and is virtually free from hydrogen fluoride.

The process of the present invention can advantageously be used in combination with distillations for the separation of the 1-chloro-1,1-difluoroethane and the hydrogen fluoride which are obtained by the hydrofluorination of vinylidene chloride or of 1,1,1-trichloroethane. After separation of the hydrogen chloride, the reaction product can be subjected directly to the first distillation. In this case, the liquid containing an auxiliary solvent can advantageously be employed directly in the separation by decantation. If it contains an adequate amount of auxiliary solvents, the reaction product can also be employed directly in the separation by decantation. In this case, the two distillations are fed solely by return of the two separated liquid phases. In both cases, the mixture to be treated according to the present invention is the mixture which has a composition similar to the azeotropic composition and is collected as the top product from the distillations.

The process according to the present invention can preferably be carried out in installations such as those which are represented schematically in FIGS. 1 to 4 of the attached drawings.

The description of these installations relate to the separation of compositions which are such that all the products fed into the first distillation contain a deficiency of hydrogen fluoride, relative to the azeotropic composition. Of course, the same installations can be used for separating compositions for which all the products fed into the first distillation contain an excess of hydrogen fluoride relative to the azeotropic composition. In this case, the points of withdrawal of the two products and the return pipes are reversed.

Turning now to FIG. 1, a composition containing hydrogen fluoride and 1-chloro-1,1-difluoroethane is introduced through a line 1 into the distillation column 2. A mixture of hydrogen fluoride and 1-chloro-1,1-difluoroethane to be treated according to the invention, which has a composition similar to the azeotropic composition, is collected continuously at a line 4. The mixture is sent through a line 5 to the condenser 6 and then through a line 7 to the decanter 9. The decanter 9 is fed through a line 8 by the liquid containing an auxiliary solvent, in accordance with the process of the present invention. The organic phase obtained in the decanter is recycled through a line 10 to the distillation column 2. 1-chloro-1,1-difluoroethane, mixed with the auxiliary solvent, is collected through a line 3 at the bottom of the column 2. The inorganic phase obtained in the decantater is sent through a line 11 into a second distillation column 13, at the bottom of which hydrogen fluoride is collected through a line 14. A mixture of hydrogen fluoride and 1-chloro-1,1-difluoroethane to be treated according to the invention, which has a composition similar to the azeotropic composition, is collected through a line 12 at the top of the column 13 and recycled through a line 5 to the condenser 6.

Figure 2:
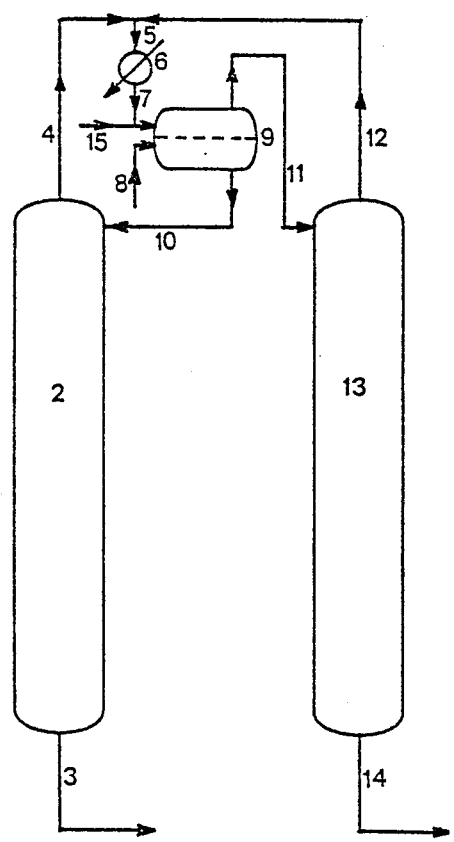
FIG. 2 is the same as FIG. 1, where the decanter is provided with an additional feedline.

FIG. 2 shows a variant of the installation represented schematically in FIG. 1, in which variant the composition of hydrogen fluoride and 1-chloro-1,1-difluoroethane is introduced through a line 15 and mixed with the azeotropic composition of hydrogen fluoride and 1-chloro-1,1-difluoroethane, which is collected at line 7, the mixture being sent to the decanter 9 in order to be treated therein according to the invention.

Figure 3:
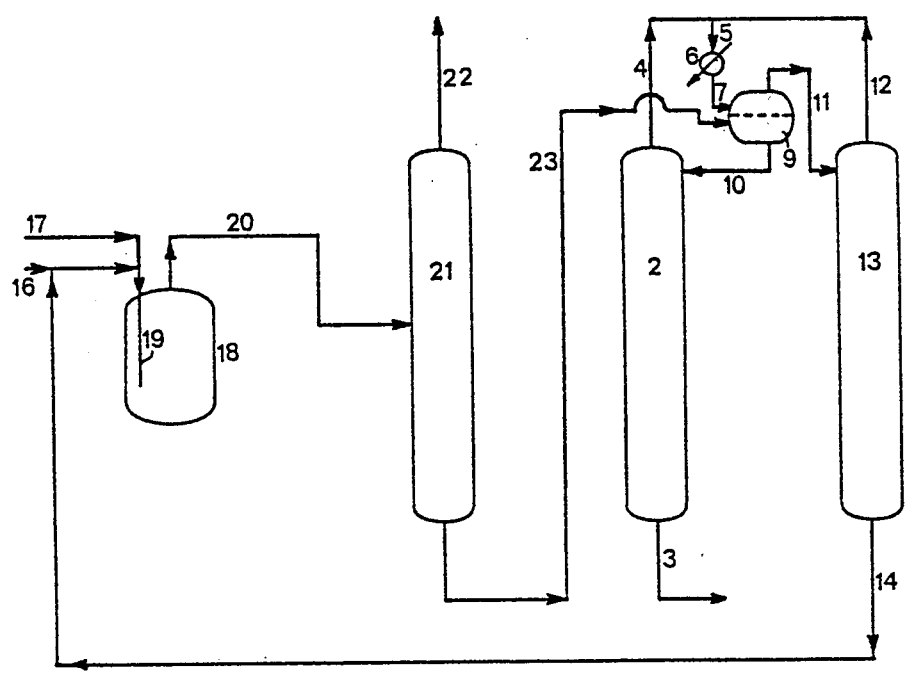
FIG. 3 shows the schematic flow diagram as shown in FIG. 2 in combination with the process flow diagram of manufacture of 1-chloro-1,1-difluoroethane by the hydrofluorination of either vinylidene chloride or 1,1,1-trichloroethane.

FIG. 3 shows a complete installation which combines that represented schematically in FIG. 2 with that for the manufacture of 1-chloro-1,1-difluoroethane by the hydro-fluorination of either vinylidene chloride or 1,1,1-trichloroethane.

The chlorohydrocarbon from a line 17, and the hydrogen fluoride, from a line 16, are introduced through line 19 into the hydrofluorination reactor 18. The composition obtained is withdrawn continuously through a line 20 and sent into the distillation column 21. The hydrogen chloride is separated from this composition at the top of the column 21. The other constituents, namely, in particular, hydrogen fluoride, 1-chloro-1,1-difluoroethane and also the 1,1-dichloro-1-fluoroethane by-product and, optionally, the unconverted chlorohydrocarbon, are sent directly through a line 23 into the decanter 9 where they act as the added liquid. Hydrogen fluoride is collected at line 14 and recycled. The mixture of halogenohydrocarbons collected at line 3 is subjected to subsequent distillations in order to separate the various constituents therefrom. The unconverted chlorohydrocarbon and 1,1-dichloro-1-fluoroethane can be recycled to the reactor or to the decanter 9.

Figure 4:
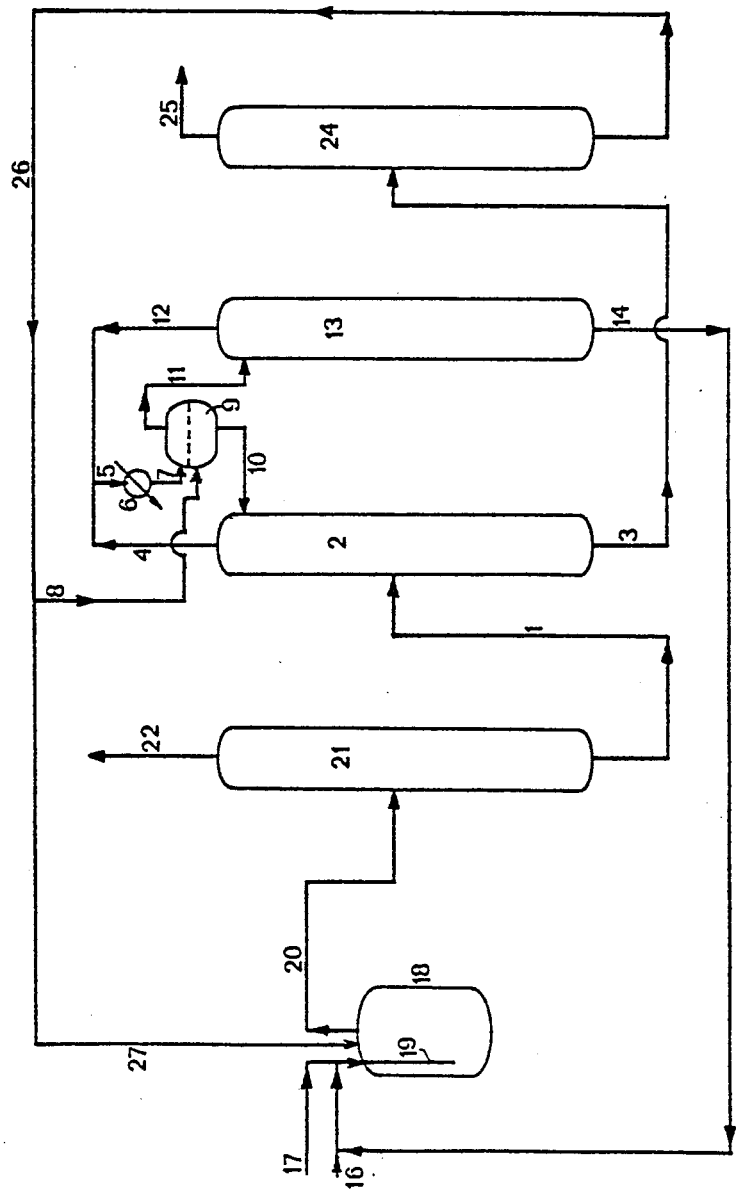
FIG. 4 shows the schematic flow diagram of yet another embodiment according to the present invention wherein distillate bottoms are further sent to yet another distillation column.

FIG. 4 shows another type of complete installation in which the composition collected at the bottom of the column 21 for the separation of the hydrogen chloride is sent through line 1 into the distillation column 2. The mixture having a composition similar to the azeotropic composition is collected continuously at line 4. 1-chloro-1,1-difluoroethane, mixed with the liquid, is withdrawn through line 3 at the bottom of the column 2 and sent into the column 24, from which 1-chloro-1,1-difluoroethane is withdrawn at the top through a line 25 and the liquid is withdrawn at the bottom through a line 26; part of this liquid is sent through line 8 to the decanter 9. The other part of the liquid is recycled through a line 27 to the reactor.

The process which forms the subject of the present invention is particularly valuable because it enables the hydrogen fluoride to be recovered, from its mixtures with 1-chloro-1,1-difluoroethane, in the anhydrous form.

By virtue of the introduction of the auxiliary solvent, the separation of the organic and inorganic phases is virtually immediate, whereas, in the absence of this solvent, the separation takes an extremely long time. Furthermore, the process according to the invention makes it possible to greatly reduce the residual content of hydrogen fluoride in the organic phase and the residual content of 1-chloro-1,1-difluoroethane in the inorganic phase. Thus, by using installations such as those represented schematically in FIGS. 1 and 2, it is possible to lower the concentration of hydrogen fluoride and 1-chloro-1,1-difluoroethane in one another to less than 1%, so as to obtain hydrogen fluoride which is virtually free from 1-chloro-1,1-difluoroethane and 1-chloro-1,1-difluoroethane which is virtually free from hydrogen fluoride. In addition, it permits a simple and efficient separation of the reaction mixture into all its constituents, without the introduction of additives which are foreign to the process.

Finally, since the auxiliary solvents according to the invention have a greater density than that of hydrogen fluoride, their introduction into the mixture to be separated facilitates the decantation.

The hydrogen fluoride which can be separated off according to the present invention can be recycled or used in other manufacturing processes, The 1-chloro-1,1-difluoroethane is commonly used for the synthesis of fluorinated monomers such as vinylidene fluoride which is itself used in the manufacture of polymers which are inert or have high resistance to chemical agents.

Embodiments are given below in order to illustrate the invention without limiting its scope.

EXAMPLES 1 and 2

Two experiments for the separation of hydrogen fluoride from its mixtures with 1-chloro-1,1-difluoroethane are carried out in the presence of 1,1-dichloro-1-fluoroethane (experiment 1) and, by way of comparison, in the absence of 1,1-dichloro-1-fluoroethane (experiment 2R). The temperature is $-20°$ C. and the pressure is 1 kg/cm$^2$.

The results obtained are presented in Table I.

TABLE I

| | COMPOSITION | |
|---|---|---|
| | EXPERIMENT 1 | EXPERIMENT 2R |
| Products employed | | |
| 1-chloro-1,1-difluoroethane | 3.1 mols | 3.7 mols |
| hydrogen fluoride | 3.3 mols | 2.5 mols |
| 1,1-dichloro-1-fluoroethane | 1.0 mols | |
| Products decanted at equilibrium | | |
| organic phase | | |
| hydrogen fluoride | 7 mol % | 18 mol % |
| 1-chloro-1,1-difluoroethane | 70 mol % | 82 mol % |
| 1,1-dichloro-1-fluoroethane | 23 mol % | — |
| inorganic phase | | |
| hydrogen fluoride | 90 mol % | 77 mol % |
| 1-chloro-1,1-difluoroethane | 8 mol % | 23 mol % |
| 1,1-dichloro-1-fluoroethane | 2 mol % | — |

Examination of the results presented in Table I shows that, by virtue of the introduction of 1,1-dichloro-1-fluoroethane into the mixture to be separated, it is possible to substantially reduce the content of organic compounds in the hydrogen fluoride and the content of hydrogen fluoride in the organic compounds.

EXAMPLE 3

This example is carried out in order to demonstrate the improvement in the separation of hydrogen fluoride and 1-chloro-1,1-difluoroethane which is achieved by virtue of the introduction of 1,1-dichloro-1-fluoroethane into the single condenser/decanter off an azeotropic distillation system with two columns.

The experiments are carried out in an installation which is analogous to that shown in FIG. 1.

A mixture containing 50 mols of hydrogen fluoride and 16 mols of 1-chloro-1,1-difluoroethane, under a pressure of 9 kg/cm$^2$, is introduced, per hour, into the column 2 through line 1. The temperature at the top of the column 2 is 48° C. The gas phase is condensed and sent into the decanter 9 which is fed with 22 mols of 1,1-dichloro-1-fluoroethane per hour.

The organic phase collected in the decanter is sent back into the column 2 and the inorganic phase is distilled in the column 13, from the top of which a gas phase, containing hydrogen fluoride and 1-chloro-1,1-difluoroethane, is withdrawn at a temperature of 48.5° C., condensed at condenser 6 and sent into the decanter 9.

The organic phase collected at line 3 at the bottom of the column 2 contains 1-chloro-1,1-difluoroethane and 1,1-dichloro-1-fluoroethane and less than 1 o/oo of hydrogen fluoride. The hydrogen fluoride collected at line 14 at the bottom of the column 13 contains less than 5 o/oo 1-chloro-1,1-difluoroethane.

It will be understood that that above description of the present invention is susceptible to various modifications, changes and adaptations, and the same are intended to be comprehended within the meaning and range of equivalents of the appended claims.

What is claimed is:

1. Process for the separation of hydrogen fluoride from its liquid mixtures with 1-chloro-1,1-difluoroethane, comprising: separating the liquid mixture by decantation to obtain a liquid organic phase enriched in 1-chloro-1,1-difluoroethane and a liquid organic phase enriched in hydrogen fluoride by adding to the mixture a liquid containing an auxiliary solvent, selected from the group consisting of 1,1-dichloro-1-fluoroethane, vinylidene chloride, 1,1,1-trichloroethane and mixtures thereof, before subjecting it to decantation.

2. Process according to claim 1, wherein the liquid added contains less than 50% by weight of 1-chloro-1,1-difluoroethane and of hydrogen fluoride.

3. Process according to claim 2, wherein the liquid added is formed exclusively of 1,1-dichloro-1-fluoroethane, vinylidene chloride and 1,1,1-trichloroethane.

4. Process according to claim 1, wherein the liquid added is employed at the rate of about 0.05 to 2.5 mols of 1,1-dichloro-1-fluoroethane, vinylidene chloride and 1,1,1-trichloroethane per mol of 1-chloro-1,1-difluoroethane.

5. Process according to claim 1, wherein the separation is carried out at a temperature below 110° C.

6. Process according to claim 1, wherein the separation is carried out at a pressure ranging from 0.8 to 30 kg/cm$^2$.

7. Process according to claim 1, wherein the liquid added is a reaction mixture originating from the hydrofluorination of vinylidene chloride.

8. Process according to claim 1, wherein the liquid added is a reaction mixture originating from the hydrofluorination of 1,1,1-trichloroethane.

9. Process according to claim 1, wherein the mixture of hydrogen fluoride and 1-chloro-1,1-difluoroethane subjected to the separation contains at least 80% by weight of hydrogen fluoride and of 1-chloro-1,1-difluoroethane.

10. Process according to claim 1, wherein the mixture of hydrogen fluoride and 1-chloro-1,1-difluoroethane subjected to the separation has a composition similar to the azeotropic composition.

11. Process according to claim 1, wherein the separation is carried out in a condenser/decanter in which the top product from two distillations is condensed, to which product the liquid is added and from which the liquid organic phase is withdrawn and fed into the reflux of one distillation and the liquid inorganic phase is withdrawn and fed into the reflux of the other.

12. Process according to claim 11, wherein the top product has a composition similar to the azeotropic composition of the mixtures of hydrogen fluoride and 1-chloro-1,1-difluoroethane.

* * * * *